United States Patent
Sugahara et al.

(10) Patent No.: US 9,974,156 B2
(45) Date of Patent: May 15, 2018

(54) CIRCULAR ACCELERATOR, CIRCULAR ACCELERATOR OPERATION METHOD, AND PARTICLE-BEAM THERAPY DEVICE

(71) Applicant: MITSUBISHI ELECTRIC CORPORATION, Chiyoda-ku, Tokyo (JP)

(72) Inventors: Kengo Sugahara, Tokyo (JP); Shuhei Odawara, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 8 days.

(21) Appl. No.: 15/110,317

(22) PCT Filed: Mar. 25, 2014

(86) PCT No.: PCT/JP2014/058179
§ 371 (c)(1),
(2) Date: Jul. 7, 2016

(87) PCT Pub. No.: WO2015/145558
PCT Pub. Date: Oct. 1, 2015

(65) Prior Publication Data
US 2016/0330827 A1     Nov. 10, 2016

(51) Int. Cl.
*H05H 13/04* (2006.01)
*A61N 5/10* (2006.01)
*H05H 7/04* (2006.01)

(52) U.S. Cl.
CPC .......... *H05H 13/04* (2013.01); *A61N 5/1077* (2013.01); *H05H 7/04* (2013.01);
(Continued)

(58) Field of Classification Search
CPC .......... A61N 2005/1087; A61N 5/1067; A61N 5/1079; A61N 2005/1074; A61N 5/1068;
(Continued)

(56) References Cited

U.S. PATENT DOCUMENTS 5,363,008 A     11/1994 Hiramoto et al.
2005/0231138 A1     11/2005 Nakanishi et al.
(Continued)

FOREIGN PATENT DOCUMENTS

EP     2 059 099 A1     5/2009
JP     5-198397 A     8/1993
(Continued)

OTHER PUBLICATIONS

The extended European Search Report dated Nov. 8, 2017, by the European Patent Office in corresponding European Patent Application No. 14887585.9-1666. (8 pages).
International Search Report (PCT/ISA/210) dated May 27, 2014, by the Japanese Patent Office as the International Searching Authority for International Application No. PCT/JP2014/058179.

*Primary Examiner* — Douglas W Owens
*Assistant Examiner* — Wei Chan
(74) *Attorney, Agent, or Firm* — Buchanan Ingersoll & Rooney PC (57) ABSTRACT

A circular accelerator that accelerates charged particles orbiting along an orbital path to a predetermined energy to perform, by deviating the path from the orbital path to an extraction path, extraction of the charged particles exceeding a stable region formed by multipole electromagnets, includes a multipole electromagnet energization control unit setting energization of the multipole electromagnets so that part of the charged particles are deviated to a discarding path other than the extraction path to discard unwanted charged particles, and then setting energization of the multipole electromagnets so that the charged particles orbiting in the
(Continued)

orbital path are deviated to the extraction path to perform extraction of the charged particles.

3 Claims, 10 Drawing Sheets

(52) U.S. Cl.
CPC .............. *A61N 2005/1087* (2013.01); *A61N 2005/1089* (2013.01); *H05H 2277/11* (2013.01)

(58) Field of Classification Search
CPC .......... A61N 2005/1089; A61N 5/1075; A61N 5/1077
USPC ........ 315/505, 507, 500, 504; 250/326, 397, 250/443.1, 492.1, 492.3
See application file for complete search history.

(56) References Cited

U.S. PATENT DOCUMENTS

| | | |
|---|---|---|
| 2009/0114852 A1 | 5/2009 | Saito et al. |
| 2012/0274242 A1* | 11/2012 | Haruna .................... H05H 7/02 315/504 |

FOREIGN PATENT DOCUMENTS

| | | |
|---|---|---|
| JP | 2003-086399 A | 3/2003 |
| JP | 2005-166689 A | 6/2005 |
| JP | 2005-332794 A | 12/2005 |
| JP | 2009-112483 A | 5/2009 |
| JP | 2011-34823 A | 2/2011 |

* cited by examiner

CIRCULAR ACCELERATOR, CIRCULAR ACCELERATOR OPERATION METHOD, AND PARTICLE-BEAM THERAPY DEVICE

TECHNICAL FIELD

The present invention relates to circular accelerators for orbiting and thereby accelerating charged particles, and particularly to a technology of extracting from the circular accelerator the charged particle beam for application to a particle beam therapy system or the like.

BACKGROUND ART

In a case of using a circular accelerator, such as a synchrotron, as a main accelerator of a particle beam therapy system, a technique commonly called "slow extraction" is employed to extract charged particles in the accelerator therefrom. In the "slow extraction", a beam-dynamically stable region (hereinafter referred to as "separatrix") is formed in the circular accelerator, and the particles are extracted by controlling the area of the separatrix. The separatrix is ordinarily formed by a multipole electromagnet. The multipole electromagnet is, for example, a sextupole electromagnet. The circular accelerator is described below taking a synchrotron as an example.

While charged particles within the separatrix keep orbiting in the synchrotron, charged particles outside the separatrix cannot keep orbiting stably, resulting in significant deviation of the particle path from the design (central) orbit. Properly designing orientation of the apexes of the separatrix (see FIGS. 3 and 5) for charged particles reaching the boundary of the separatrix to pass through the extraction path allows the charged particles to be extracted from the synchrotron.

Various methods of transferring charged particles within a separatrix toward the boundary thereof have been proposed. In a classical method, strength of a quadrupole electromagnet is varied to change the horizontal tune of charged particles orbiting in the synchrotron, whereby the area of the separatrix is decreased, resulting in transferring the particles toward the boundary of the separatrix. In another method, a radio frequency electric field including a resonance frequency component is applied to the radio frequency electrode to increase the Courant-Snyder invariants of charged particles, thus performing extraction while transferring the particles toward the boundary of the separatrix (for example, Patent Document 1). In still another method, the momentum of charged particles orbiting in the synchrotron is varied during acceleration by the radio frequency accelerating cavity, whereby the tune of the particles is changed and the area of separatrix is decreased, thus performing extraction (for example, Patent Document 2).

In any methods, the invariant parameter called the Courant-Snyder invariant exits for accelerated charged particles, and no unstable extraction occurs in an ideal physical design. In an actual compact synchrotron for a particle beam, however, the Courant-Snyder invariants of charged particles orbiting in the synchrotron increase with elapsed time by being subject to influences of constituent devices, such as ripple noise of the power source for the bending electromagnets and distortion of and noise components of the electric field formed in the radio frequency accelerating cavity.

In other words, a phenomenon occurs in which charged particles that are supposed to exist originally within the separatrix are unexpectedly transferred to the outside of the separatrix owing to disturbance factors. Note that the "elapsed time" here means a time required from injection to acceleration, a waiting time for the extraction enable signal in using for particle beam therapy, or the like.

Before extraction, the area of the separatrix in the phase space is ordinarily set to be significantly larger than the maximum area of the Courant-Snyder invariants of orbiting particles (by no energization of the extraction multipole electromagnet), to keep a condition of no extraction even when there exist disturbance factors. On reception of the extraction enable signal, preparation for extraction is made in which the area of the separatrix is made equal to the maximum value of the Courant-Snyder invariants of the charged particles by a method such as for energizing, for example, the sextupole electromagnet, to start gradually the extraction. In a case where a Courant-Snyder invariant distribution of the charged particles extends over a wider range than an estimate Courant-Snyder invariant distribution owing to disturbance factors so far, however, a much larger number of particles per unit time than ordinary slow extraction—this is referred to as "spike"—may extracted in an preparation period for the extraction only by slightly decreasing the separatrix area. Moreover, characteristics (width and momentum) of the beam extracted in the period may in some cases differ significantly from those in the design condition.

In a scanning irradiation proposed for particle beam therapy systems recently applied to cancer treatment (for example, Patent Document 3), temporal stability of the intensity waveform of a particle beam used for the irradiation is highly requested more than before because the irradiation needs to be controlled spot by spot. A particle beam, i.e., charged particles extracted during the above-described spike period, has an extreme peak intensity, thus causing irradiation doses to be uncontrollable. Moreover, the particle beam is of poor quality, for example, its parameters, such as a beam diameter, are different from the design parameters. Since the particle beam during the spike period is thus uncontrollable for the irradiation, it is desired not to irradiate a target with such a beam.

Techniques for removing the spike has been proposed, in which the particle beam extracted from the accelerator during the spike period is removed, for example, at a damper by being deflecting the traveling direction so as not to irradiate a target or the particle beam is removed in the accelerator by narrowing the separatrix (stable region) during a preparation period for extraction so as not to be extracted from the accelerator (for example, Patent Document 4).

PRIOR ART DOCUMENT

Patent Document

Patent Document 1: JP1993-198397 A
Patent Document 2: JP2003-086399 A
Patent Document 3: JP2005-332794 A
Patent Document 4: JP2009-112483 A

SUMMARY OF THE INVENTION

Problem that the Invention is to Solve

In order to remove a particle beam by deflecting the traveling direction of the beam extracted from the accelerator, however, an external device such as a deflecting electromagnet (kicker electromagnet) that operates at high speed needs to be provided to a beam delivery line downstream of the synchrotron. Moreover, in a method for the removing in the accelerator only narrowing the stable region, the path of unwanted charged particles cannot be controlled.

The present invention is made to resolve such problems and aimed at providing a circular accelerator that has a simple configuration and is capable of controlling the path of unwanted charged particles and thereby allows for extracting a particle beam having no spike.

Means for Solving the Problem

According to the present invention, a circular accelerator that accelerates charged particles orbiting along an orbital path to a predetermined energy to perform, by deviating the path from the orbital path to an extraction path, extraction of the charged particles exceeding a stable region formed by multipole electromagnets, the circular accelerator, includes a multipole electromagnet energization control unit controlling energization of the multipole electromagnets wherein the multipole electromagnet energization control unit sets energization of the multipole electromagnets so that part of the charged particles are deviated to a discarding path other than the extraction path to discard unwanted charged particles, and then sets energization of the multipole electromagnets so that the charged particles orbiting in the orbital path are deviated to the extraction path to perform extraction of the charged particles.

Advantages of the Invention

According to the present invention, a synchrotron can be provided that has a simple configuration and is capable of controlling the path of unnecessary charged particles and thereby allows for extracting a particle beam having no spike.

EMBODIMENTS FOR CARRYING OUT THE INVENTION

Embodiment 1

Figure 1:
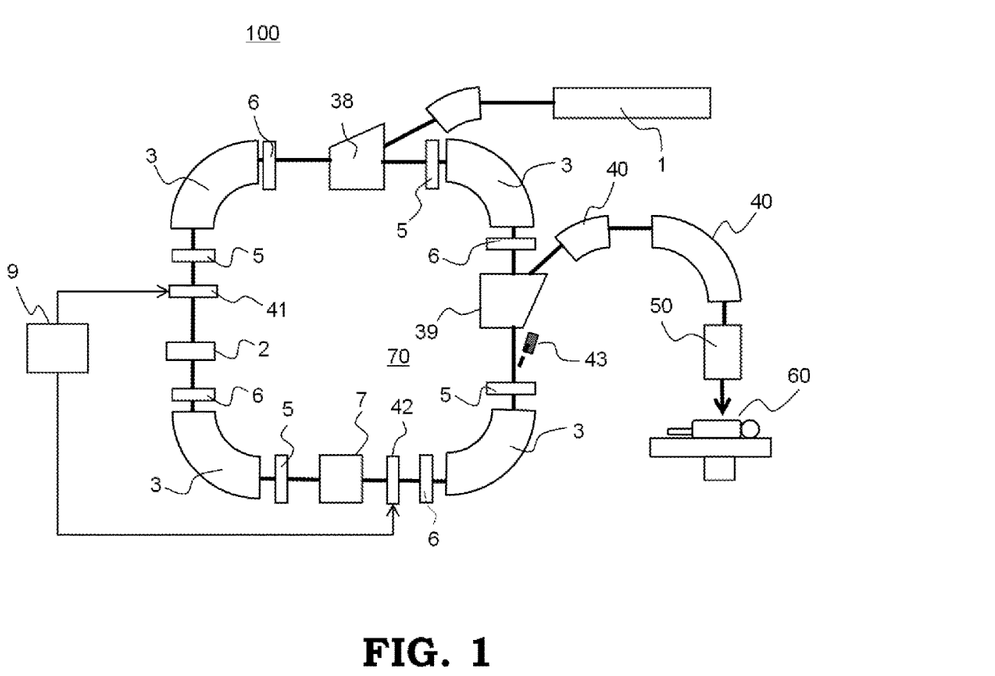
FIG. 1 is a block diagram showing a component arrangement of a particle beam therapy system including a circular accelerator according to Embodiment 1 of the present invention.

FIG. 1 is a block diagram showing a component arrangement of a particle beam therapy system including a circular accelerator according to Embodiment 1 of the present invention. A main accelerator here is a synchrotron, a typical circular accelerator. Charged particles accelerated to a sufficient energy by a pre-accelerator 1 including an ion beam generator are injected into a synchrotron ring 100 through an injector unit 38, to be accelerated in the synchrotron ring 100 to a target energy. The charged particles are accelerated by a radio frequency accelerating cavity 2 in the synchrotron ring 100. The synchrotron ring 100 is provided with bending electromagnets 3 for orbiting the charged particles along an orbital path to form a charged particle beam. The charged particles accelerated in the synchrotron ring 100 are excited into the third-order resonance before extraction by sextupole electromagnets employed as a first multipole electromagnet 41 and a second multipole electromagnet 42, respectively, whereby a separatrix is formed. The betatron oscillation is divided into a stable region (inside the separatrix) and a resonance region (outside the separatrix). That is, the first and the second multipole electromagnets 41, 42 constitute a region dividing device for dividing the betatron oscillation of the charged particles orbiting along the orbital path into the stable region and the resonance region. Quadrupole electromagnets 5 are used for adjusting the betatron frequency and the area of the separatrix. Energization of the first and the second multipole electromagnets 41, 42 is controlled by a multipole electromagnet energization control unit 9. In the following description, the first and the second multipole electromagnets 41, 42 are regarded as the first sextupole electromagnet 41 and the second sextupole electromagnet 42, respectively.

In the synchrotron ring 100, the charged particles have a central momentum uniquely determined from magnetic fields of the bending magnets 3 and are distributed around the center momentum. In this condition, the central momentum is varied, for example, using the radio frequency accelerating cavity 2 to narrow the stable region (the area of the separatrix) of the betatron oscillation, so that the charged particle is expelled into the resonance region. The charged particles entering into the resonance region increase in amplitude in the x-direction by the resonance. When the charged particles reach a range sensitive to the electric field of, for example, an extraction electrode 7, the particles are guided by electric field force generated by the extraction electrode 7, so that the path of the particles is changed, i.e., deviated from the orbital path to an extraction path. Then, the path is deflected outwardly by an extraction electromagnet mounted to an extraction port 39, so that the charged particles are extracted from the synchrotron. That is, the extraction electrode 7 and the extraction electromagnet mounted to the extraction port 39 constitute an extraction unit 70.

Figure 2:
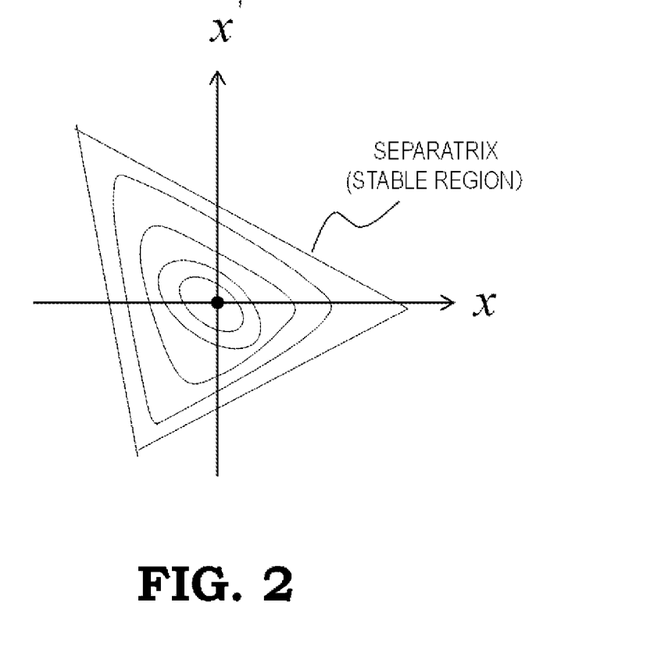
FIG. 2 is a schematic diagram illustrating an example of a state of charged particles in the circular accelerator.
Figure 3:
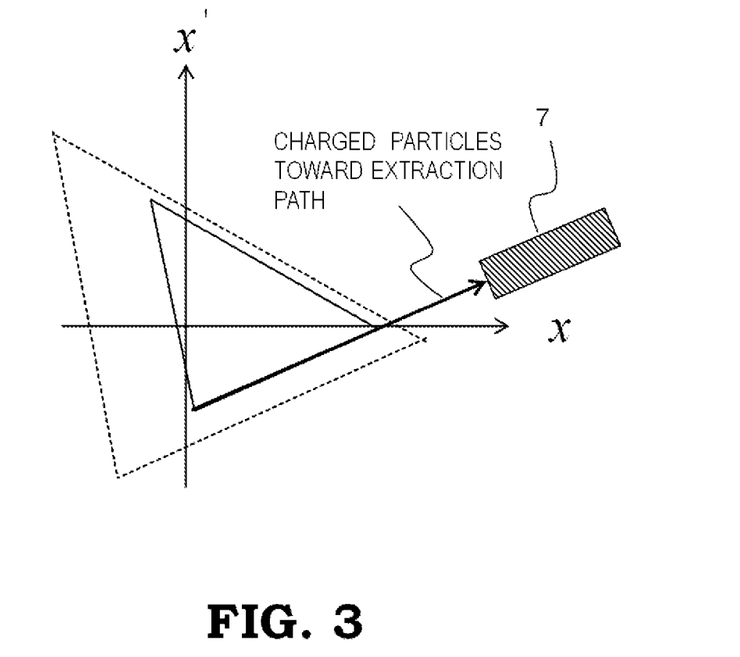
FIG. 3 is a schematic diagram illustrating an example of extraction of the charged particles from the circular accelerator.

The above operation is explained with reference to the drawings. Viewing from a direction (hereinafter, referred to as a lateral direction) orthogonal to the traveling direction of the beam, the horizontal axis represents a position x and the vertical axis represents an inclination x' of the path. The beam maintains stably the orbital motion with a betatron oscillation (exactly speaking, while oscillating stably around the design orbital path without diverging). In a case of, for example, the third-order resonance, the first and the second sextupole electromagnets 41, 42 in the synchrotron are adjusted to excite the third-order oscillation when extracting the beam, whereby the betatron oscillation is divided into the stable region and the resonance region. In other words, a triangular separatrix is formed within the boundary between the stable region and the unstable region of oscillation as shown in FIG. 2. In this condition, varying the frequency of voltage applied to the radio frequency accelerating cavity causes the momentum of the particles to change, whereby the tune thereof is changed. Then, as shown in FIG. 3, the separatrix region for acceleration indicated by the broken-line triangle is changed at beam extraction to narrow the stable region indicated by the solid-line triangle when extraction, so that part of the charged particles are expelled into the unstable region. The charged particles expelled into the unstable region outside the separatrix drastically increases in amplitude by the resonance. At this time, for example, providing an electrode to generate an electric field at the hatched position of the extraction electrode 7 shown in FIG. 3 allows the path of the charged particles increasing in amplitude and traveling to the position to be changed from the orbital path to the extraction path by the force of the electric field. The charged particles transferred to the extraction path are largely deflected by the extraction electromagnet mounted to the extraction port 39 and finally extracted from the accelerator.

The charged particle beam extracted from the synchrotron ring 100 is guided to a location where the beam is utilized through a beam delivery line ordinarily constituted with some electromagnets 40 and vacuum ducts. FIG. 1 shows an example of utilizing the charged particle beam for a particle beam therapy system. The charged particle beam is guided to an irradiation apparatus 50 through the beam delivery line. And then, the irradiation apparatus 50 scanningly irradiates a diseased site of a patient 60 with the beam focused to a pencil beam, i.e., performs scanning irradiation.

Figure 4:
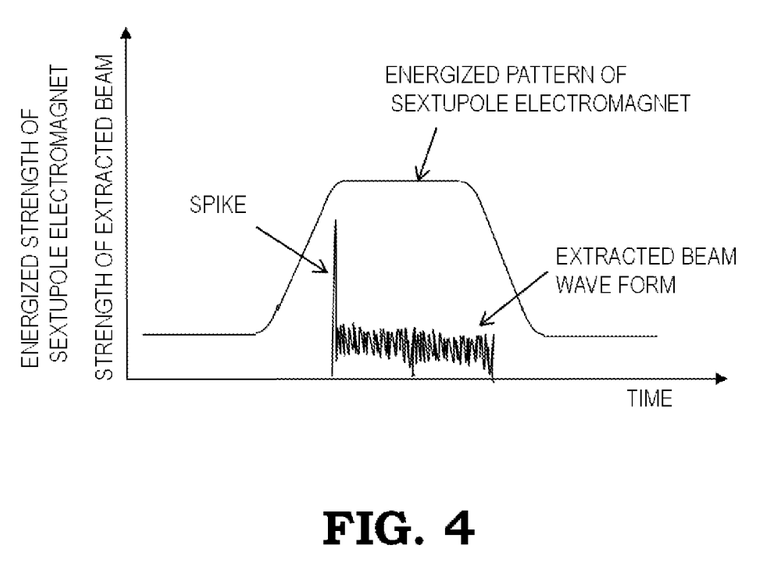
FIG. 4 is a schematic diagram illustrating an example of beam waveform extracted from a conventional circular accelerator.

The orientation of the apexes of the triangular separatrix shown in FIGS. 2 and 3 is determined by controlling energization of the first and the second sextupole electromagnets 41, 42 by the multipole electromagnet energization control unit 9. For beam extraction, the orientation of the apexes of the triangular separatrix are adjusted so that the charged particles expelled into the unstable region travels toward the aperture guiding to the extraction electrode, as shown in FIG. 3. Before extraction, the area of the separatrix is increased so that even when the particles are distributed such that maximum values in their Courant-Snyder invariant distribution spread over a wider range than the estimated Courant-Snyder invariant distribution, the particles are kept not entering into the unstable region. In order to start extraction from this condition, the area of the separatrix is decreased by varying the central momentum using, for example, the radio frequency accelerating cavity 2, then particles whose Courant-Snyder invariants are larger than the estimated Courant-Snyder invariant are expelled all at once toward the extraction electrode to enter the extraction path, resulting in extraction of a beam having a spike-like output intensity. The extracting operation is illustrated in FIG. 4. The sextupole electromagnets are energized for the beam extraction, so that the orientation of the triangular separatrix—the traveling path of the charged particles to be extracted—is directed toward the extraction electrode, i.e., to the extraction path, as shown in FIG. 3. At the start of extraction, the charged particles whose Courant-Snyder invariants are larger than the design value are extracted all at once, resulting in formation of the spike-like extraction beam waveform. After that, charged particles having the design Courant-Snyder invariant are extracted and the extracted beam has a predetermined design intensity. The above is an operation of a conventional synchrotron during the beam extraction.

Figure 5:
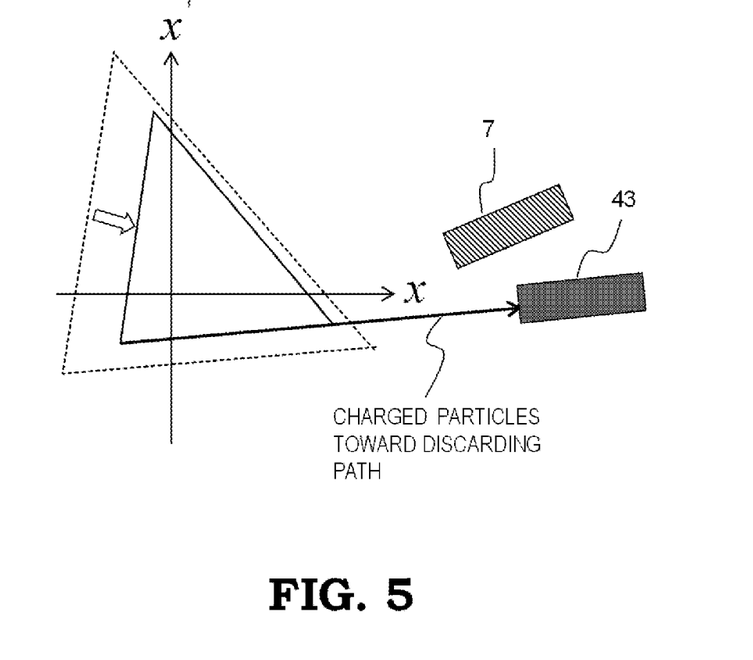
FIG. 5 is a schematic diagram illustrating an operation of the circular accelerator during a first extraction preparing operation period according to Embodiment 1.

In contrast to the above, an operation according to the present invention will be now described with reference to FIGS. 5 and 6. In the present invention, after an accelerating operation period is completed and the charged particles reach a predetermined energy, the multipole electromagnet energization control unit 9 sets energization of the first and the second sextupole electromagnets 41, 42 so that the orientation of the apexes of the separatrix is adjusted to the direction shown in FIG. 5. At this time, the area of the separatrix is set so that charged particles whose Courant-Snyder invariants are larger than the estimated Courant-Snyder invariant remain also within the separatrix indicated by the broken-line triangle in FIG. 5. After the orientation of the separatrix is set, the area of the separatrix is decreased so that charged particles whose Courant-Snyder invariants are within the design value remain within the separatrix indicated by the solid-line triangle in FIG. 5. By this operation, unwanted poor-quality charged particles, which have Courant-Snyder invariants larger than the design value, are deviated from the orbital path to a discarding path different from the extraction path, as shown in FIG. 5.

The unwanted charged particles deviated to the discarding path are removed without extracted from the synchrotron. Preferably, designing the positional relationship between the discarding path and a damper 43 such that the unwanted charged particles in the discarding path are directed toward the damper 43, the unwanted charged particles are removed by the damper 43. In this way, energization of the multipole electromagnets is controlled so that the orientation of the separatrix is adjusted for the unwanted charged particles to be deviated to the discarding path different from the extraction path. Since the travelling direction of the unwanted charged particles can be thus adjusted by controlling energization of the multipole electromagnets, the unwanted charged particles can be discarded by being removed at the damper 43. Controlling the direction of the unwanted charged particles brings about many merits compared to a case of no control. For example, forming the damper 43 of a sufficient thick shield material allows for suppressing radiation, which is generated by secondary scattering from the damper, to a sufficiently low energy. Moreover, while heat is generated at a portion the unwanted charged particles impinging on, only damper 43 may be cooled by impingement on the damper 43. Furthermore, a design can be made such that the unwanted charged particles do not impinge on a member such as resin that degrades by impingement of charged particles.

Figure 6:
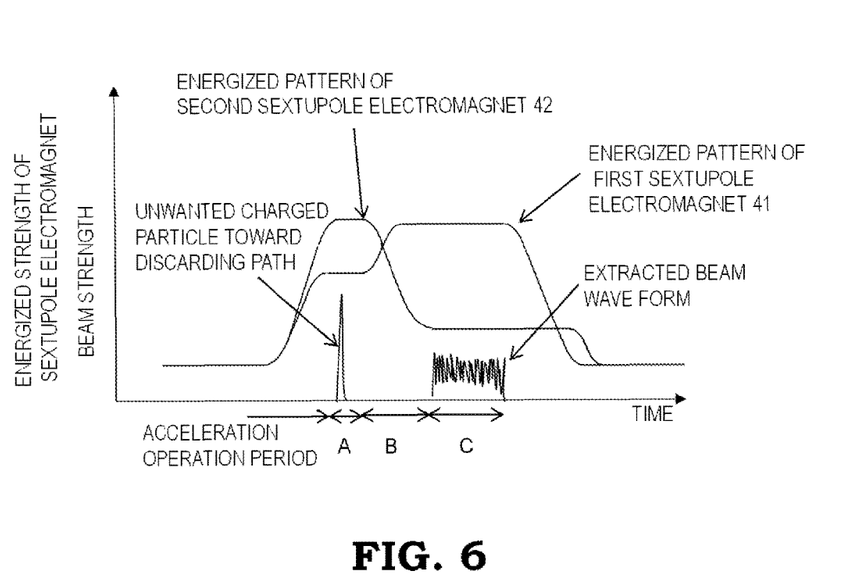
FIG. 6 is a diagram for explaining an operation of the circular accelerator according to Embodiment 1.

The operation period of discarding the unwanted charged particles is indicated by "A" in FIG. 6 and referred to as a first extraction preparing operation period. Specifically, the unwanted charged particles are deviated from the orbital path to the discarding path to be removed by the damper 43 during the first extraction preparing operation period A. In this way, during the first extraction preparing operation period A, the orientation of the separatrix is set to the direction that causes the charged particles outside the separatrix to be deviated from the orbital path to the discarding path. The damper 43 for removing the unwanted charged particles deviated to the discarding path may be mounted, for example, on the inner wall of the duct forming the orbital path of the synchrotron. The position of the damper depends on lattice design of the synchrotron and the orientation of the apexes of the separatrix. The orbital path of the particles reaching the boundary of the separatrix increases outwardly during three turns. The damper is mounted at a position the particles impinge on in the three-turn orbiting, however, the position should be chosen where the particles do not impinge during the injection period and the acceleration period. In addition, the beam damper is generally formed of metal.

Figure 7:
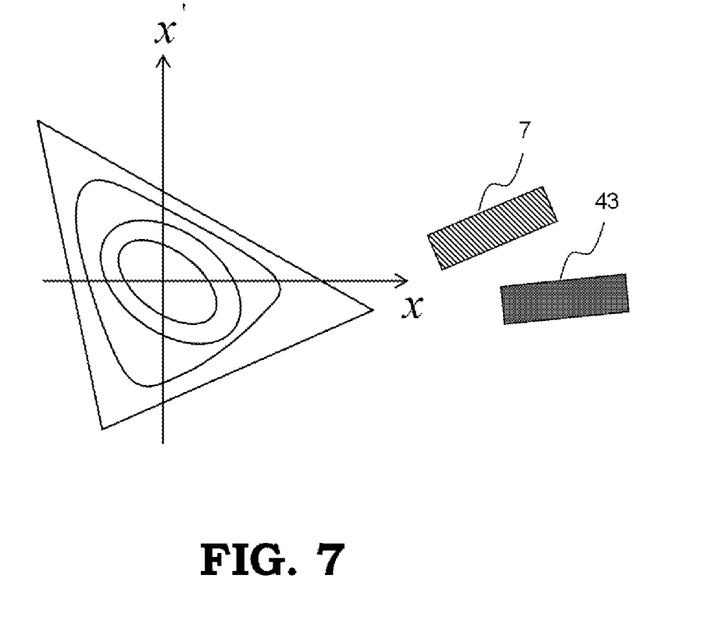
FIG. 7 is a schematic diagram illustrating an operation of the circular accelerator during a second extraction preparing operation period according to Embodiment 1.
Figure 8:
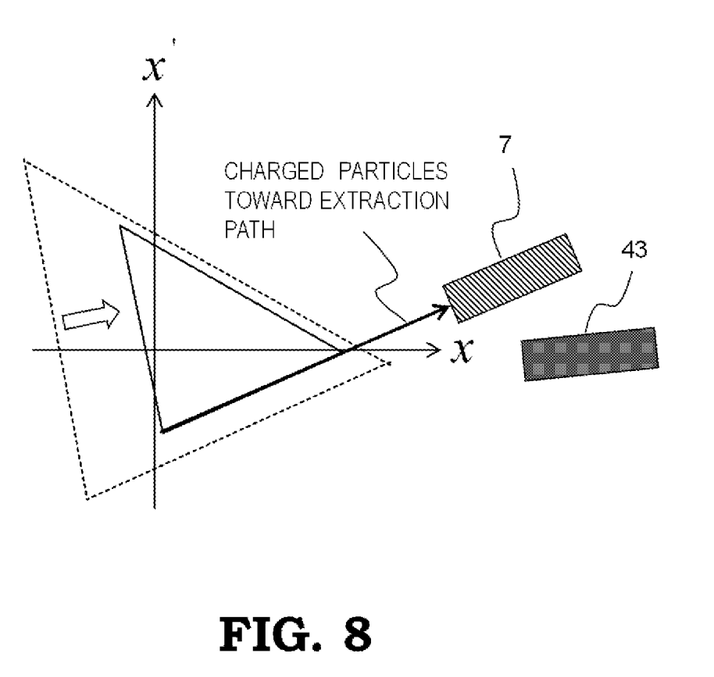
FIG. 8 is a schematic diagram illustrating an operation of the circular accelerator during an extracting operation period according to Embodiment 1.

After the unwanted particles are removed such as by the damper 43, the area of the separatrix is increased again so that the charged particles whose Courant-Snyder invariants are within the design value are not deviated from the orbital path. Since it is unclear at design time that how much intensity of unwanted beam occurs, the operation procedure is adjusted in the beam adjustment period. A waveform such as shown in FIG. 4 is acquired with a beam spill monitor, and the period A is gradually increased while measuring the magnitude of spike shown in FIG. 6. No spike structure is observed in the extracted beam spill as the period A is increased sufficiently. Then, energization of the first and the second sextupole electromagnets 41, 42 is varied to set the orientation of the triangular separatrix, as shown in FIG. 7, so that the travelling path of the charged particles expelled toward the outside of the separatrix is directed toward the extraction electrode 7, i.e., directed to the extraction path when the area of the separatrix is decreased. This operation period is indicated by "B" in FIG. 6 and referred to as a second extraction preparing operation period B. After the orientation of the separatrix is set, by gradually decreasing the area of the separatrix as shown in FIG. 8, charged particles whose Courant-Snyder invariants are within the design value—charged particles permitting an irradiation dose and the like to be controlled—enter gradually into the unstable region outside the separatrix, whereby the charged particles are deviated from the orbital path and are expelled toward the extracting electrode 7, and then extracted from the synchrotron through the extraction path by the extraction electromagnet mounted to the extraction port 39. This operation period is indicated by "C" in FIG. 6 and referred to as an extracting operation period C. During the extracting operation period C, the design beam with no spike can be extracted.

As described above, during the first extraction preparing operation period A, energization of the first and the second sextupole electromagnets 41, 42 is set so that the orientation of the separatrix is directed differently form that of the separatrix during the extracting operation period C, and the area of the separatrix is once decreased at the same time. During the first extraction preparing operation period A, the unwanted charged particles are deviated from the orbital path to the discarding path to be removed by the damper 43 or the like. During the second extraction preparing operation period B subsequent to the first extraction preparing operation period A, the area of the separatrix is increased and the setting of energization of the first and the second sextupole electromagnets 41, 42 is changed to adjust the orientation of the separatrix so that travelling path of the charged particles to be expelled toward the outside of the separatrix is directed to the extraction path during the extracting operation period C. During the extracting operation period C subsequent to the second extraction preparing operation period B, the area of the separatrix is gradually decreased, whereby the particle beam, which is flux of charged particles being uniform in quality, is extracted from the synchrotron to be utilized for treatment or the like.

Note that, while the triangular separatrix is formed using sextupole electromagnets as the multipole electromagnets in the above description, the number of poles of the multipole electromagnets is not limited to six. For example, a fourth-order resonance generated by employing octupole electromagnets forms a quadrangular separatrix. While the separatrix thus has a polygonal shape corresponding to the number of poles of the multipole electromagnets, energization of the first and the second multipole electromagnets 41, 42 may be controlled to adjust the orientation of the polygonal separatrix so that the charged particles expelled toward the outside of the separatrix are deviated to the discarding path different from the extraction path during the first extraction preparing operation period A and so that the charged particles expelled toward the outside of the separatrix are deviated to the extraction path during the extracting operation period C. In addition, beam extraction is not limited to use of the method of varying frequency of the radio frequency accelerating cavity. Furthermore, the beam extraction method may be different between during the period A and during the period C.

Embodiment 2

While Embodiment 1 describes the method of expelling poor-quality charged particles into the discarding path by decreasing the area of the separatrix during the first extraction preparing operation period A, a method such as disclosed in Patent Document 1 may also be used, in which a radio frequency electric field including a frequency component resonating with the radio frequency electrodes is applied to increase the Courant-Snyder invariants of the charged particles, to consequently transfer and expel the particles toward the outside of the separatrix.

Figure 9:
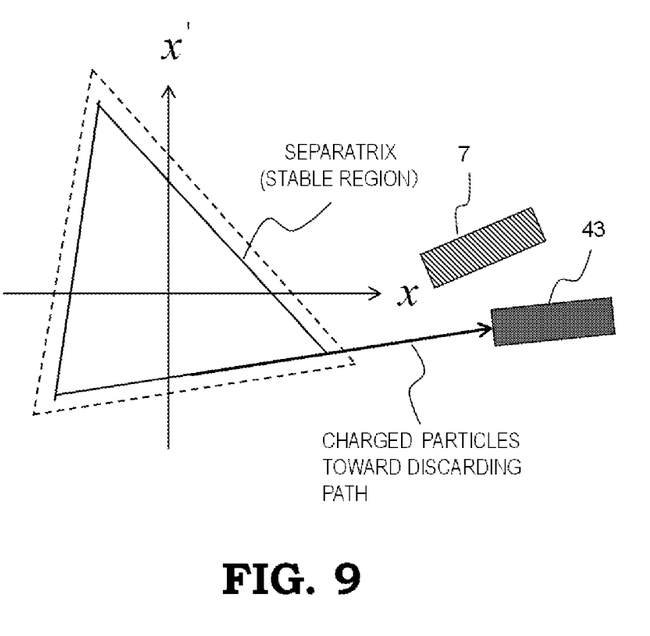
FIG. 9 is a schematic diagram illustrating an operation of a circular accelerator during a first extraction preparing operation period according to Embodiment 2 of the present invention.
Figure 10:
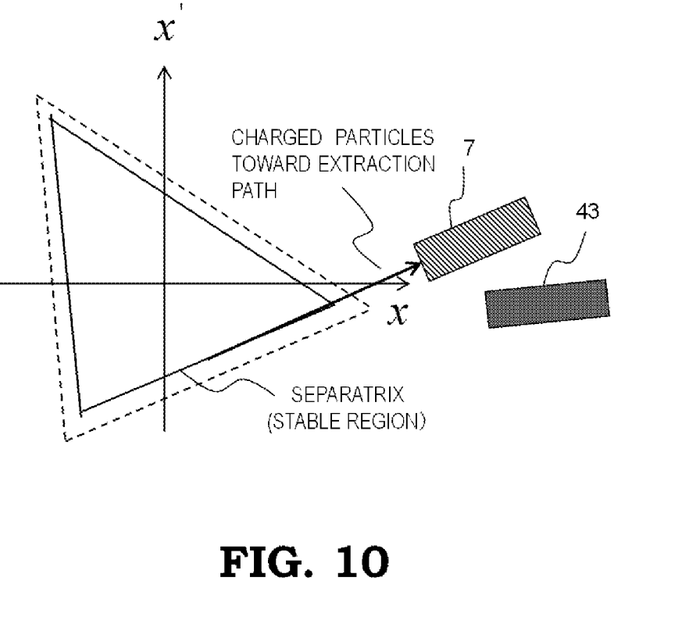
FIG. 10 is a schematic diagram illustrating an operation of the circular accelerator during an extracting operation period according to Embodiment 2.

The energization of the multipole electromagnets is set during the first extraction preparing operation period A to adjust the orientation of polygonal separatrix is directed so that the charged particles expelled toward the outside of the separatrix are deviated toward the discarding path, as shown in FIG. 9. After setting, a radio frequency electric field including a frequency component resonating with the radio frequency electrodes is applied to increase the Courant-Snyder invariants of the charged particles, so that the region in which the unwanted charged particles originally having large Courant-Snyder invariants are distributed is extended to the region indicated by the broken line in FIG. 9. The unwanted charged particles expelled toward the outside of the separatrix and deviated to the discarding path are removed, for example, by the damper 43 or the like. During the second extraction preparing operation period B, application of the radio frequency electric field including the frequency component resonating with the radio frequency electrodes is stopped to restore the Courant-Snyder invariants of the charged particles, and energization of the multipole electromagnets is set at the same time to adjust the orientation of the separatrix so that the charged particles outside the separatrix are directed to the extraction electrode 7, i.e., to the extraction path, as shown in FIG. 10. And then, during the extracting operation period C, the radio frequency electric field including the frequency component resonating with the radio frequency electrodes is applied again to increase the Courant-Snyder invariants of the charged particles, i.e., to extend the charged particle distribution to the region indicated by the broken line in FIG. 10, so that the charged particles resultantly existing outside the separatrix are extracted from the synchrotron through the extraction path. In addition, stopping of the beam during the period B is implemented not only by the method of stopping the application of the radio frequency electric field. There exists another method in which the area of the separatrix is sharply increased by means of a fast quadrupole electromagnet or the like.

Thus, good-quality charged particles with no spike can be extracted during the extracting operation period C.

While the above description is made taking as an example a synchrotron, a typical circular accelerator, the present invention can also be applied to a circular accelerator other than a synchrotron as long as the circular accelerator forms a separatrix by exciting charged particles orbiting in the accelerator by mean of multipole electromagnets.

REFERENCE NUMERALS

9: multipole electromagnet energization control unit;

39: extraction port;

41: first multipole electromagnet (sextupole electromagnet);

42: second multipole electromagnet (sextupole electromagnet);

50: irradiation apparatus;

100: synchrotron (circular accelerator);

A: first extraction preparing operation period;

B: second extraction preparing operation period; and

C: extracting operation period.

The invention claimed is:

1. A circular accelerator operating method that includes accelerating charged particles orbiting along an orbital path to a predetermined energy during an accelerating operation and then extracting the charged particles exceeding a stable region formed by multipole electromagnets, the circular accelerator operating method comprising:
   a first extraction preparing operation of controlling a stable region formed by the multipole electromagnets for part of the charged particles to exceed the stable region to be removed in the circular accelerator;
   a second extraction preparing operation subsequent to the first extraction preparing operation, of extending the stable region and of varying energization of the multipole electromagnets so that orientation of a polygonal shape of the stable region is directed differently from orientation of the stable region during the first extraction preparing operation after; and
   an extracting operation subsequent to the second extraction preparing operation, of gradually narrowing the stable region to extract the charged particles from the circular accelerator.

2. The circular accelerator operating method of claim 1, wherein two electromagnets that are the multipole electromagnets are placed apart from each other along the orbital path, and the two electromagnets are controlled so that orientation of the polygonal stable region differs between in the first extraction preparing operation and in the extracting operation.

3. The circular accelerator operating method of claim 1, wherein the charged particles exceeding the stable region are removed by being impinged on a damper during the first preparing operation.

* * * * *